(12) United States Patent
Scalzo et al.

(10) Patent No.: US 11,504,268 B2
(45) Date of Patent: Nov. 22, 2022

(54) WOUND TREATMENT SYSTEM

(71) Applicant: Ethicon, Inc., Somerville, NJ (US)

(72) Inventors: Howard Scalzo, Kenilworth, NJ (US); Xintian Ming, Bridgewater, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 458 days.

(21) Appl. No.: 16/019,814

(22) Filed: Jun. 27, 2018

(65) Prior Publication Data

US 2020/0000630 A1    Jan. 2, 2020

(51) Int. Cl.
| | | |
|---|---|---|
| *A61F 7/02* | (2006.01) | |
| *A61F 7/00* | (2006.01) | |
| *A61F 13/02* | (2006.01) | |
| *A61F 13/00* | (2006.01) | |
| *A61F 15/00* | (2006.01) | |

(52) U.S. Cl.
CPC ............. *A61F 7/02* (2013.01); *A61F 7/007* (2013.01); *A61F 13/00063* (2013.01); *A61F 13/0203* (2013.01); *A61F 15/008* (2013.01); *A61F 2007/0001* (2013.01); *A61F 2007/0078* (2013.01); *A61F 2007/0226* (2013.01); *A61F 2007/0261* (2013.01); *A61F 2013/002* (2013.01); *A61F 2013/00182* (2013.01); *A61F 2013/00195* (2013.01)

(58) Field of Classification Search
CPC .... A61F 7/00; A61F 7/007; A61F 7/02; A61F 2007/001; A61F 2013/00187; A61F 13/00063; A61F 13/023; A61F 13/0266; A61L 2300/00

USPC ............ 602/41–48, 2, 14, 54; 604/304, 306
See application file for complete search history.

(56) References Cited

U.S. PATENT DOCUMENTS

| | | | |
|---|---|---|---|
| 5,518,730 A | * | 5/1996 | Fuisz .................... A61L 17/005 424/426 |
| 6,293,917 B1 | | 9/2001 | Augustine et al. |
| 6,406,448 B1 | * | 6/2002 | Augustine ............... A61F 7/007 602/2 |

(Continued)

FOREIGN PATENT DOCUMENTS

| | | | | |
|---|---|---|---|---|
| FR | 1527887 A | 6/1968 | | |
| WO | WO-2004032704 A2 | * | 4/2004 | ....... A61B 17/06114 |
| WO | 2004107816 A1 | 12/2004 | | |

OTHER PUBLICATIONS

Josephine J. Braid, et al.; "The antibacterial activity of triclosan-impregnated storage boxes against Staphylococcus aureus, Escherichia coli, Pseudomonas aeruginosa, Bacillus cereus and Shewanella putrefaciens in conditions simulating domestic use"; Journal of Antimicrobial Chemotherapy; vol. 49; pp. 87-94; (2002).

(Continued)

*Primary Examiner* — Rachael E Bredefeld
*Assistant Examiner* — Trisha Talapatra
(74) *Attorney, Agent, or Firm* — David R. Crichton (57) ABSTRACT

A disposable dressing forms a compartment around and above a wound site and a volatile antimicrobial compound is allowed to sublimate/evaporate into the compartment. A heating element is included in the dressing, with heat stimulating wound healing and simultaneously accelerating sublimation/evaporation of the antimicrobial compound.

18 Claims, 3 Drawing Sheets

(56) References Cited

U.S. PATENT DOCUMENTS

| | | | | |
|---|---|---|---|---|
| 6,465,709 B1* | 10/2002 | Sun | ......................... | A61F 7/034 602/41 |
| 7,014,630 B2 | 3/2006 | Rosati | | |
| 2002/0172709 A1* | 11/2002 | Nielsen | ............... | A61L 28/0038 424/445 |
| 2003/0069529 A1* | 4/2003 | Augustine | ........... | A61F 13/0203 602/48 |
| 2006/0271020 A1* | 11/2006 | Huang | ............... | A61M 5/14232 604/890.1 |
| 2008/0033329 A1* | 2/2008 | Downs | .................... | A61L 15/46 602/41 |
| 2013/0345649 A1* | 12/2013 | Stockley, III | ........... | A61F 7/034 604/304 |
| 2015/0297877 A1* | 10/2015 | Pelkus | .................. | A61M 16/16 128/203.12 |
| 2017/0231823 A1* | 8/2017 | Zawoy | .............. | A61F 13/00068 604/23 |
| 2018/0289556 A1* | 10/2018 | Levy | ..................... | A61F 15/004 |
| 2018/0318137 A1* | 11/2018 | Donda | .................... | A61F 13/02 |

OTHER PUBLICATIONS

R. J. Lewis, et al.; "Inhibition of bacteria on agar surfaces by vapour phase triclosan"; Journal of Antimicrobial Chemotherapy; vol. 52; Issue 2; pp. 314-315; (2003).
Extended European Search Report EP Application No. 19826658.7 dated Mar. 3, 2022.

* cited by examiner

WOUND TREATMENT SYSTEM

FIELD

Disclosed herein is a wound treatment system and a method of wound treatment that delivers anti-microbial agents, accelerates wound healing, and minimizes contact of the wound with potentially contaminating elements.

ENVIRONMENT

Each year, patients undergo a vast number of surgical procedures in the United States. Current data shows about twenty-seven million procedures are performed per year. Post-operative or surgical site infections ("SSIs") occur in approximately two to three percent of all cases. This amounts to more than 675,000 SSIs each year.

The occurrence of SSIs is often associated with bacteria that colonize wounds sites subsequent to surgery. During a surgical procedure, bacteria from the surrounding atmosphere may enter the surgical site and deposit in the wound. Additionally, bacteria can be spread during repeated opening and closing of the wound site when changing dressings or the like. Such bacterial contamination of the wound may lead to infection of and trauma to the patient. Accordingly, SSIs may significantly increase the cost of treatment to patients.

Additionally, the tissue at the wound site can be affected by hypothermia due to the low temperature of the operating room, and due to disruptions in the blood flow to the wound site caused by the removal of tissue and surgical injury to the tissue.

During surgery the temperature of the operating room is maintained at levels that provide comfort of the surgical staff. Due to the additional clothing worn and the inherent stress of the surgery on the doctors, nurses and other surgical staff, the operating room temperature is maintained at temperatures near 23° C. (73.4° F.). This lower temperature as well as other factors of surgery including anesthesia, can cause the surgical patient to be hypothermic. This condition of hypothermia, commonly defined as <96.8° F. (36° C.) for core body temperature has been associated with significant morbidity and mortality. Also, there has been a threefold increase in the frequency of surgical site infections is reported in colorectal surgery. "Unintended Perioperative Hypothermia", Stuart R. Hart, MD, Brianne Bordes, Jennifer Hart, MD, Daniel Corsino, MD, and Donald Harmon, MD, Ochsner J. 2011 Fall; 11(3): 259-270. Kurz A. "Physiology of thermoregulation", *Best Pract Res Clin Anaesthesiol.* 2008; 22(4):627-644.

Thermal post-surgical treatment of wound sites is beneficial to healing due to the increased blood perfusion. The increase in blood flow to the wound also increases oxygen tension, which has been shown to aid in wound healing and may reduce the risk of infection.

The use of a heat patch previously described can provide the necessary warming to the surgical site area to allow the body temperature to increase above the 96.8° F. hypothermia condition back to a normal range or a normothermia state. This normothermia state allows for the significant reduction of the morbidity and mortality that is associated with hypothermia and will reduce the frequency of surgical site infections.

It would be advantageous to develop a non-contacting wound treatment system that provides thermal treatment and greater oxygen tension to the site of a wound, delivers a wound treatment agent, and helps to prevent microbial infections.

SUMMARY

Presented herein is a wound treatment system, comprising a body structured and arranged to surround a wound area, the body having an opening above the wound area, a cover attached to the body and covering the opening, the cover suspended above the wound area, the opening and the cover forming an enclosed and empty wound treatment compartment, an autonomous heating element incorporated into the body or into the cover, and a medically useful agent evaporating or sublimating at an accelerated speed at a temperature from about 40 to about 80° C., the medically useful agent in fluid communication with the compartment.

In one form, the amount of the agent is effective to inhibit bacterial infection of the wound.

In another form, the heating element is structured and arranged to heat the agent to a temperature sufficient to inhibit bacterial infection of the wound.

In yet another form, the medically useful agent is located on the heating element, or is located close enough to the heating element to receive radiant heat from the heating element.

In another form, the cover is a transparent or semi-transparent film, or a transparent or semi-transparent dome.

Advantageously, the medically useful agent is an antimicrobial agent, such as one selected from the group consisting of halogenated hydroxyl ethers, acyloxydiphenyl ethers, and combinations thereof.

In another form, the medically useful agent is impregnated in a strip of an inert carrier, and can be triclosan impregnated in a strip of melt-spun polymer.

In yet another form, dimensions of the enclosed wound treatment compartment are adjustable to accommodate wounds of different dimensions.

Also presented herein is a method of wound treatment, comprising (i) enclosing a wound area with a wound treatment system comprising a body structured and arranged to surround a wound area, the body having an opening above the wound area, a cover attached to the body and covering the opening, the cover suspended above the wound area, the opening and the cover forming an enclosed and empty wound treatment compartment, an autonomous heating element incorporated into the body or into the cover, and a medically useful agent evaporating or sublimating at an accelerated speed at a temperature from about 40 to about 80° C., the medically useful agent in fluid communication with the compartment, (ii) activating the heating element, thereby heating the medically useful agent, (iii) evaporating or sublimating portions of the medically useful agent to cause vapors of the medically useful agent to fill the enclosed wound treatment compartment, and (iv) contacting the wound with the medically useful agent vapors.

In one form, activating of the heating element provides radiant heat to the wound area.

In some forms, the cover is a transparent or semi-transparent film or a transparent or semi-transparent dome.

In yet another form, the medically useful agent is an antimicrobial agent selected from the group consisting of halogenated hydroxyl ethers, acyloxydiphenyl ethers, and combinations thereof.

In particular, the medically useful agent is triclosan impregnated in a strip of melt-spun polymer.

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Described herein is a non-contacting wound treatment system that provides thermal treatment and greater oxygen tension to the site of a wound, delivers an antimicrobial agent to the surface of the wound in a non-contact fashion through the gas or vapor phase above the wound, and helps to prevent microbial infections.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

According to the present disclosure, a disposable dressing forms a compartment around and above a wound site and a volatile antimicrobial compound is allowed to sublimate/evaporate into the compartment. A heating element is included in the dressing, with heat stimulating wound healing and simultaneously accelerating sublimation/evaporation of the antimicrobial compound. Antimicrobial vapor saturates the enclosed compartment and deposits from the vapor phase onto the wound tissue. The antimicrobial agent present in the vapor phase within the enclosed compartment is continuously regenerated by continued heating of the antimicrobial agent and is continuously deposited onto the wound.

Figure 1:
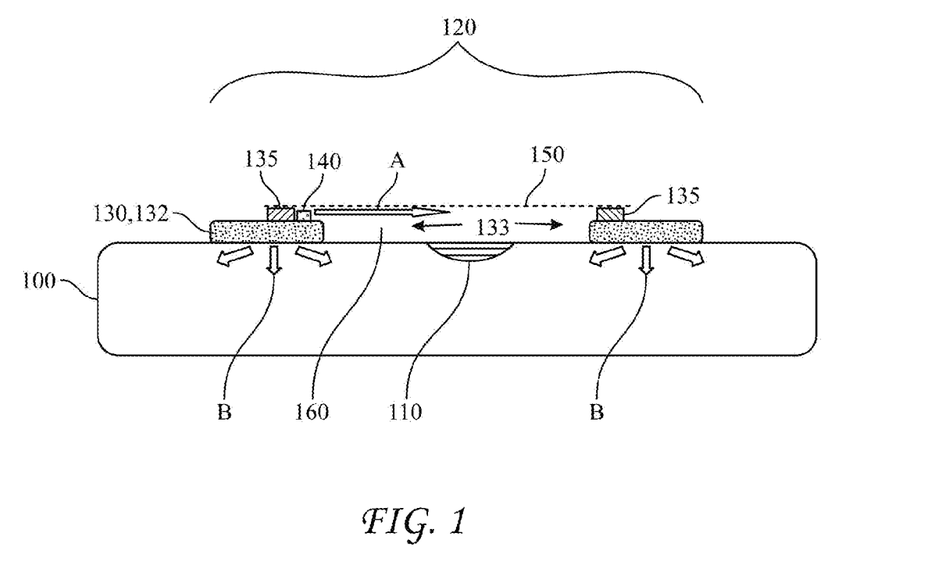
FIG. 1 is a side cross-sectional view of a first form of a wound treatment system.
Figure 4A:
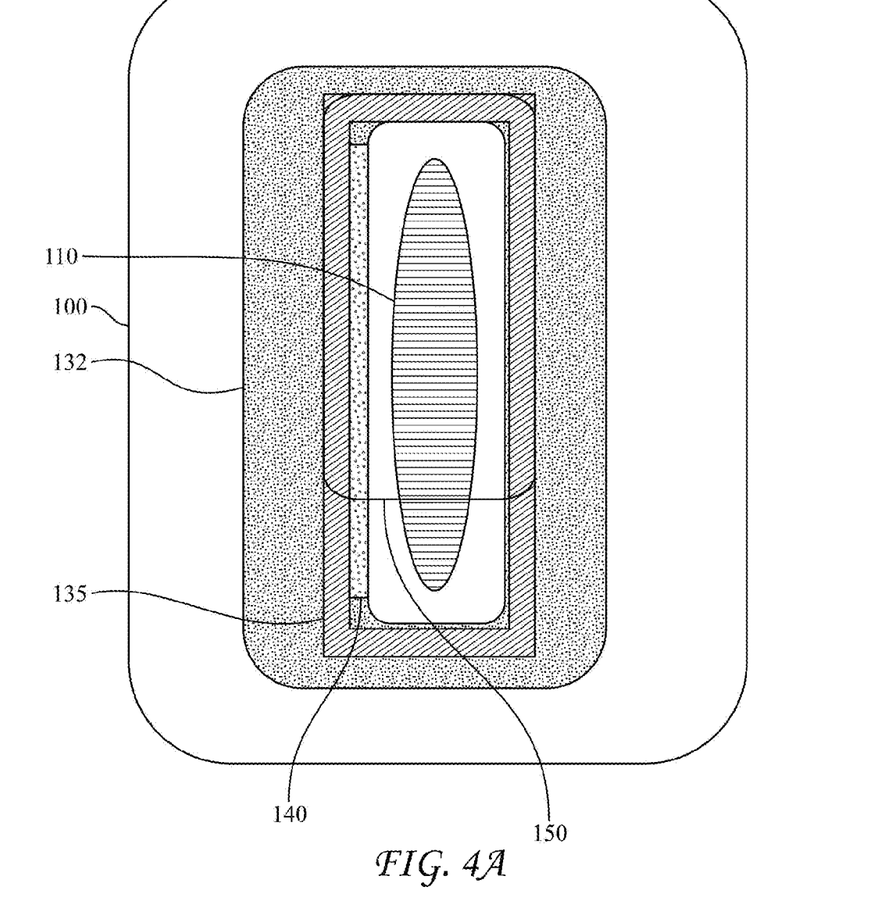
FIG. 4A is a top view of the first form of a wound treatment system.
Figure 4B:
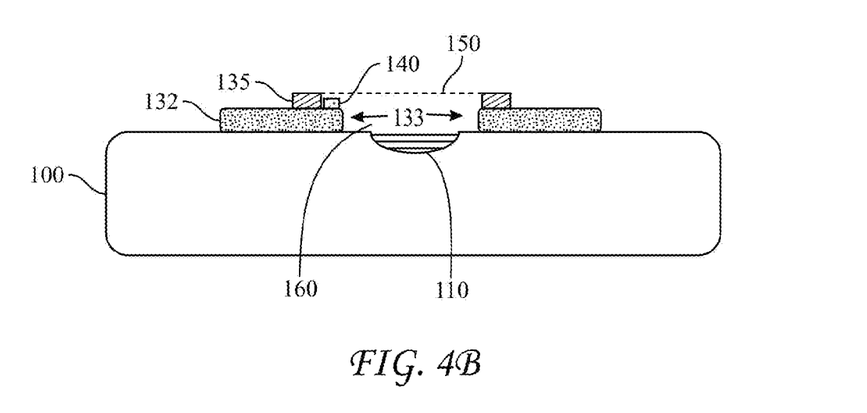
FIG. 4B is a side cross-sectional view of FIG. 4A.

A first form of the presently disclosed wound treatment system is illustrated in FIGS. 1 and 4. The wound treatment system 120 includes a body 130, which is configured to surround a wound 110, such as a surgical incision or the like. Body 130 can be constructed of any biocompatible material, most preferably polymeric material typically used to form dressings and wound covering devices and known to a skilled artisan. The materials can be natural or synthetic polymers or combinations thereof, such as cellulose, polyesters, hydrocolloids, polyethylene, polypropylene, gelatin, and similar. A portion of body 130 can comprise an absorbent material, such a fibrous sponge, to absorb and remove wound exudates. Preferably, an adhesive (not shown) is disposed on at least a portion of the body 130 which is in contact with tissue or skin 100. Any suitable adhesive known in the art of bandages or adherent wound dressings can be utilized, preferably pressure sensitive adhesive, such as acrylics-based pressure sensitive adhesive, to ensure body 130 is immobilized on and securely attached to tissue or skin 100. The body 130 has an opening 133 above the wound area and a film cover 150, attached to the body 130 covering the opening. Film cover 150 can be transparent or non-transparent, but it is preferably transparent or semi-transparent. In this form, the cover 150 is a film suspended above the wound 110. The film can be made of any suitable biocompatible polymer, such as polyesters, polyethylene, polypropylene, PVC, PET, and similar, most preferably having enough transparency so that the conditions of the wound 110 can be observed through film cover 150. In some embodiments, film is impermeable or has very low permeability to water vapor and is substantially non-porous. The opening 133 and the cover 150 form an enclosed and empty wound treatment compartment 160. An autonomous heating element 132 is incorporated into the body 130, which provides heat in direction B to both the underlying skin 100 and to an easily evaporating or sublimating medically useful agent 140, such as an antimicrobial agent, in fluid communication with the compartment 160.

Any medically useful volatile agent 140 can be used, that can evaporate or sublimate at a faster rate at temperatures slightly above the normal body temperature of 36.6° C. and saturate wound treatment compartment 160 with vapors of agent 140. Preferably, agent 140 has limited or very minor evaporation or sublimation at ambient temperature such as 20° C., but accelerated evaporation or sublimation at temperatures above 40 or 45 or 50 or 60° C. In some embodiments, agent 140 has evaporation or sublimation rate that is at least 2 or 5 or 10 or 100 times higher at 45 or 50 or 60° C. than at 20° C. In one embodiment, agent 140 comprises triclosan. In another embodiment, agent 140 comprises ethanol with additives rendering it less volatile at ambient temperature. In this form, the medically useful agent 140 is located on the body 130 containing heating element 132 and receives radiant heat sufficient to cause evaporation or sublimation in direction A, into the wound treatment compartment 160. In one form, an optional spacer 135 is located between the body 130 and the cover film 150. The spacer also can be a thermal insulating spacer positioned between the tissue or skin 100 and the heating element 132, thus enabling higher temperature of the heating element supplied to the medically useful agent but lower temperature on the surface of the skin or tissue, preventing potential burns.

Advantageously, the medically useful agent 140 is an antimicrobial agent, which has a low evaporation or sublimation temperature, preferably from about 25 to about 80° C. The temperature and the antimicrobial agents are selected to provide for sufficient evaporation or sublimation of the antimicrobial agent in order to provide for sufficient antimicrobial action. In one embodiment, the partial vapor pressure of the antimicrobial agent at 50° C. is at least about $1 \times 10^{-4}$ mm Hg, or even at least about $5 \times 10^{-4}$ mm Hg. The antimicrobial agent can be one selected from the group consisting of halogenated hydroxyl ethers, acyloxydiphenyl ethers, and combinations thereof. In one form, the antibacterial agent is triclosan. The medically useful agent 140 can be impregnated in a strip of an inert carrier, such as triclosan impregnated in or deposited on a strip of paper or a strip of a melt-spun polymer, such as melt-spun high density polyethylene, available as Tyvek®, from DuPont de Nemours Company of Wilmington, Del.

The incorporation of heating element 132 also provides heat to the patient and wound site to help maintain normothermia and increase oxygen tension to the wound site.

Figure 2:
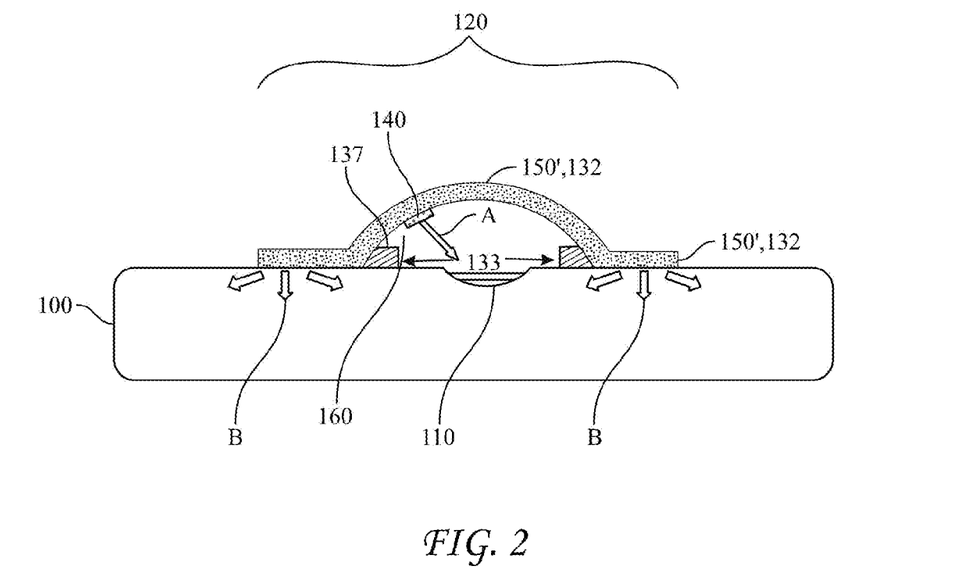
FIG. 2 is a side cross-sectional view of a second form of a wound treatment system.

In another form illustrated in FIG. 2, the cover can be in the form of a transparent or semi-transparent dome 150', which provides for a larger treatment compartment 160. Dome 150' can be made of any suitable biocompatible polymer, such as polyesters, polyethylene, polypropylene, PVC, PET, and similar, most preferably having enough transparency so that the conditions of the wound 110 can be observed through dome 150. In all forms, the enclosed treatment compartment 160 comprises space not filled with any material immediately above the wound 110, preventing any elements of the wound treatment system 120 from directly touching the wound 110 and causing irritation, potential contamination, disruption of wound healing, and painful removal. The presently disclosed non-contact wound treatment system 120 makes contact with the skin or tissue 100 only in the areas surrounding the wound, and does not contact the wound itself.

In FIG. 2, the heating element 132 is incorporated into the body 130 similarly to the embodiment of FIG. 1, or alternatively/additionally into covering dome 150'; the antimicrobial source 140 is located on a bottom surface of dome 150', receiving radiant heat therefrom and causing evaporation or sublimation into vapor, which travels in direction A toward the wound 110 and generally fills the compartment 160. An optional absorbent pad 137, such as a foam or sponge, can be provided around the wound 110 to absorb exudates from the wound.

Figure 3:
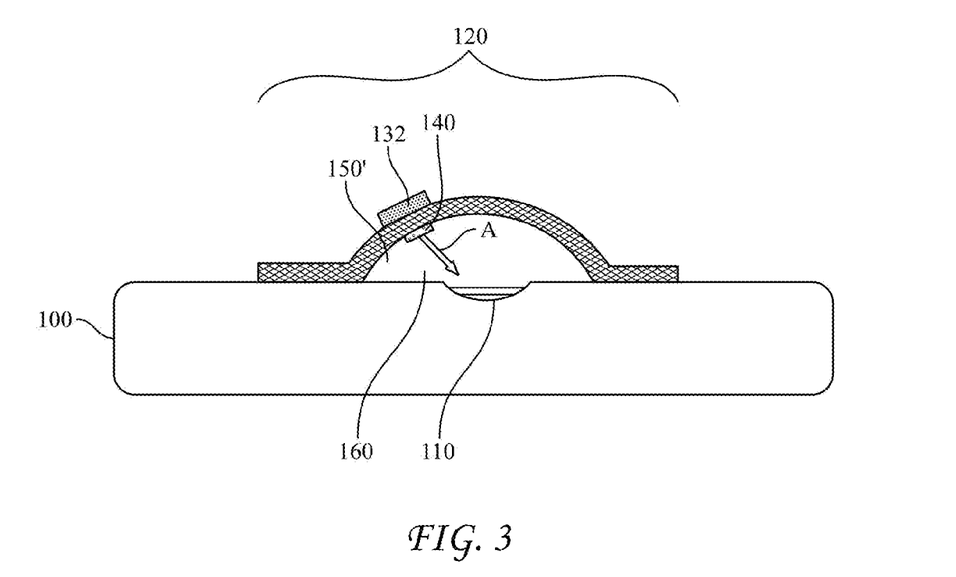
FIG. 3 is a side cross-sectional view of a third form of a wound treatment system.

FIG. 3 illustrates another form of the wound treatment system 120 in which the heating element 132 is disposed only on a portion of the underlying cover dome 150', opposite the antimicrobial source 140, which receives radiant heat from the heating element 132. The radiant heat also is directed into and through treatment compartment 160 and toward wound site 110 along with the antimicrobial vapor in direction A.

Advantageously, in some embodiments the dimensions of the enclosed wound treatment compartment 160 are adjustable to accommodate wounds of different dimensions. In such embodiments body 130 has areas of stretchability that allow the body 130 to be expanded/extended around a larger wound, with cover film 150 and/or dome 150' having enough slack or stretchability to accommodate expansion/extension of body 130.

FIGS. 4A and 4B are top and side cross-sectional views of the first form of a wound treatment system, with agent 140 shown disposed in an elongated strip form on one side of the heating element 132. In other embodiments (not shown) agent 140 can be disposed also symmetrically on opposite side of the heating element 132. Alternatively, agent 140 can be disposed as a singular spot deposit, or as a plurality of discrete deposits, or around the whole circumference of compartment 160.

In some forms, at least a part of the body of the wound treatment system 120 comprises a self-contained heating element 132, which upon activation generates heat and supplies heat to the skin or tissue 100 surrounding the wound 110, providing thermal treatment to the area immediately surrounding the wound site, increasing blood perfusion and oxygen tension, and improving healing and reducing infection. No heat is supplied directly (via conductive heat transfer) to the wound 110. The heating element 132 can be an air activated heating pack, based on iron powder, active carbon, water, and salt, with an air-permeable enclosure, as known in the art. Other types of heating elements are also suitable, such as heat packs utilizing heat of crystallization, electrically heated heat packs (particularly battery-powered), etc.

Also presented herein is a method of wound treatment, comprising (i) enclosing a wound with a wound treatment system comprising a body structured and arranged to surround a wound, the body having an opening above the wound area, a cover attached to the body and covering the opening, the cover suspended above the wound, the opening and the cover forming an enclosed and empty wound treatment compartment, an autonomous heating element incorporated into the body or into the cover, and an easily evaporating or sublimating medically useful agent in fluid communication with the compartment, (ii) activating the heating element, thereby heating the medically useful agent, (iii) evaporating or sublimating portions of the medically useful agent to cause vapors of the medically useful agent to fill the enclosed wound treatment compartment, and (iv) contacting the wound with the medically useful agent vapors.

In use, the medically useful agent is present in the vapor phase within the enclosed treatment compartment 160 and is continuously regenerated by continued heating of the medically useful agent 140 and by continuous deposition on the wound. The temperature of the heating element 132 in contact with or directed to the medically useful agent 140 is from about 40 to about 60° C., or even from about 45 to about 50° C. In this way, the medically useful agent 140 is supplied to the wound surface 110 throughout the treatment from the gas or vapor phase, constantly replenishing any medically useful agent that is absorbed by the tissue, carried away by exudates, dissolved, etc. The wound treatment system 120 can provide heat and supply the medically useful agent for an extended period of time, such as 4 hours, 8 hours, 12 hours, 24 hours, or 48 hours.

Alternatively, the medically useful agent 140 is supplied to the wound surface at the beginning of the treatment as the heating element heats up, and all of the medically useful agent 140 evaporates or sublimates from the medically useful agent element at the beginning of the treatment, i.e. within 5-30 minutes from the heating element reaching its operating temperature, or within 30-60 minutes from activating the heating element. The medically useful agent evaporated or sublimated from the antibacterial element then fills the enclosed treatment compartment 160 and deposits on the wound from the gas phase.

Specific forms will now be described further by way of example. While the following examples demonstrate certain forms of the subject matter disclosed herein, they are not to be interpreted as limiting the scope thereof, but rather as contributing to a complete description.

containing about 6 log CFU/ml *S. aureus*. For testing, from 1 to 8 triclosan strips, each containing 9 mg of triclosan, were positioned on heating elements in proximity to inoculated Petri dishes. The assembly was covered creating an enclosed compartment around the inoculated Petri dishes, with triclosan patches within thusly formed compartment on the heating elements but not in contact with the inoculated Petri dishes. The inoculated Petri dishes were taken out after 3 hr and 17 hour exposure at ambient temperature (of which heating packs provided about 7 hours of heat) and incubated at 37° C. for 24 hr to allow the bacterial colonies, if any, to grow and be evaluated. Controls tested included the same model without any heating elements; heating elements in a system with no triclosan; no heating, no triclosan for confirming inoculation and bacterial growth, no heating no triclosan no inoculation for confirming agar was not contaminated.

TABLE

| Test # | # heating elements | Setting # triclosan patches | Inoculating | description | Bacterial Growth after 37° C. incubation | |
|---|---|---|---|---|---|---|
| | | | | | Exposure to wound treatment system: 3 hr | Exposure to wound treatment system: Additional 17 hr |
| 1 | 4 | 8 | Yes | Heat + triclosan effect on bacterial growth | NONE | NONE |
| 2 | 4 | 4 | Yes | Heat + triclosan effect on bacterial growth | NONE | NONE |
| 3 | 4 | 2 | Yes | Heat + triclosan effect on bacterial growth | NONE | NONE |
| 4 | 4 | 2 | Yes | Heat + triclosan effect on bacterial growth | NONE | NONE |
| 5 | 0 | 8 | Yes | No Heat + triclosan effect on bacterial growth | Partial growth | NONE |
| 6 | 0 | 4 | Yes | No Heat + triclosan effect on bacterial growth | Partial growth | Minimal growth |
| 7 | 0 | 2 | Yes | No Heat + triclosan effect on bacterial growth | Full growth | Full growth |
| 8 | 4 | 1 | Yes | Heat + triclosan effect on bacterial growth | NONE | NONE |
| 9 | 0 | 1 | Yes | No Heat + triclosan effect on bacterial growth | Full growth | Full growth |
| 10 | 4 | 0 | Yes | Heat + No triclosan effect on bacterial growth | Full growth | Full growth |
| 11 | 0 | 0 | Yes | CONTROLS: No Heat No triclosan | Full growth | Full growth |
| 12 | 0 | 0 | Yes | CONTROLS: No Heat No triclosan | Full growth | Full growth |
| 13 | 0 | 0 | Yes | CONTROLS: No Heat No triclosan | Full growth | Full growth |
| 14 | 0 | 0 | No | CONTROLS: No Heat No triclosan No inoculation | NONE | NONE |
| 15 | 0 | 0 | No | CONTROLS: No Heat No triclosan No inoculation | NONE | NONE |

Examples

The experimental data were obtained with a model air-activated heating elements (7 Hour Hand Warmers, Grabber, Grand Rapids, Mich.) surrounding a model wound represented by inoculated Petri dishes with 5 ml of 45C TSA agar Tests of inventive devices tests #1-4, 8 had 4 heating elements and from 1 to 8 triclosan patches and demonstrated full inhibition of bacterial growth. Controls tests #5-7, 9-15 had either no heating and/or no triclosan and/or no inoculation. Tests #5-7, 9, 11-15 had no heating; Tests #10-15 had no triclosan; Tests 14-15 had no inoculation.

Comparison of control tests 5-7, 10-15 to inventive device tests 1-4, 8 indicates that in presence of heat elements even 1 strip of triclosan was sufficient to show full bactericidal effect on *S. aureus* with vapor transfer of triclosan.

Without heat elements, most tests indicated lack of antibacterial effect. However, one test, test #5, with maximum 8 strips of triclosan, showed full antibacterial effect after 17 hours, but still insufficient effect (partial growth) after 3 hours.

The experimental data demonstrated that heating elements enabled vapor phase delivery of triclosan to the model wound surface.

PCT1. A wound treatment system, comprising a body structured and arranged to surround a wound area, said body having an opening above the wound area, a cover attached to the body and covering the opening, said cover suspended above the wound area, said opening and said cover forming an enclosed and empty wound treatment compartment, an autonomous heating element incorporated into the body or into the cover, and a medically useful agent evaporating or sublimating at an accelerated speed at a temperature from about 40 to about 80° C., said medically useful agent in fluid communication with the compartment.

PCT2. The wound treatment system of paragraph PCT1, wherein the amount of said agent is effective to inhibit bacterial infection of said wound.

PCT3. The wound treatment system of paragraphs PCT1 or PCT2, wherein the heating element is structured and arranged to heat said agent to a temperature sufficient to inhibit bacterial infection of said wound.

PCT4. The wound treatment system of any preceding PCT paragraph, wherein the medically useful agent is located close enough to the heating element to receive radiant heat from the heating element.

PCT5. The wound treatment system of any preceding PCT paragraph, wherein the medically useful agent is located on the heating element.

PCT6. The wound treatment system of any preceding PCT paragraph, wherein the cover is a transparent or semi-transparent film.

PCT7. The wound treatment system of any of paragraphs PCT1 to PCT5, wherein the cover is a transparent or semi-transparent dome.

PCT8. The wound treatment system of any preceding PCT paragraph, wherein the medically useful agent is an antimicrobial agent, such as one selected from the group consisting of halogenated hydroxyl ethers, acyloxydiphenyl ethers, and combinations thereof.

PCT9. The wound treatment system of any preceding PCT paragraph, wherein the medically useful agent is impregnated in a strip of an inert carrier.

PCT10. The wound treatment system of any preceding PCT paragraph, wherein the medically useful agent is triclosan impregnated in a strip of melt-spun polymer.

PCT11. The wound treatment system of any preceding PCT paragraph, wherein dimensions of the enclosed wound treatment compartment are adjustable to accommodate wounds of different dimensions.

PCT12. A method of wound treatment, comprising (i) enclosing a wound area with a wound treatment system comprising a body structured and arranged to surround a wound area, the body having an opening above the wound area, a cover attached to the body and covering the opening, the cover suspended above the wound area, the opening and the cover forming an enclosed and empty wound treatment compartment, an autonomous heating element incorporated into the body or into the cover, and a medically useful agent evaporating or sublimating at an accelerated speed at a temperature from about 40 to about 80° C., said medically useful agent in fluid communication with the compartment, (ii) activating the heating element, thereby heating the medically useful agent, (iii) evaporating or sublimating portions of the medically useful agent to cause vapors of the medically useful agent to fill the enclosed wound treatment compartment, and (iv) contacting the wound with the medically useful agent vapors.

PCT14. The method of paragraph PCT13, wherein activating the heating element provides radiant heat to the wound area.

PCT15. The method of paragraphs PCT13 or PCT14, wherein the cover is a transparent or semi-transparent film.

PCT16. The method of paragraphs PCT13 or PCT14, wherein the cover is a transparent or semi-transparent dome.

PCT17. The method of any of paragraphs PCT13 to PCT16, wherein the medically useful agent is an antimicrobial agent selected from the group consisting of halogenated hydroxyl ethers, acyloxydiphenyl ethers, and combinations thereof.

PCT18. The method of any of paragraphs PCT13 to PCT17, wherein the medically useful agent is triclosan impregnated in a strip of melt-spun polymer.

INDUSTRIAL APPLICABILITY

The systems and methods disclosed herein are applicable to the health care industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

We claim:

1. A wound treatment system, comprising:
a body structured and arranged to surround a wound area, said body having an opening above the wound area;
a cover attached to the body and covering the opening, said cover suspended above the wound area;
said opening and said cover forming an enclosed and empty wound treatment compartment;
an autonomous heating element incorporated into the body or into the cover; and
a medically useful agent evaporating or sublimating at an accelerated rate above normal body temperature of about 40° C. to about 80° C.
said medically useful agent in fluid communication as a gas or vapor with the wound treatment compartment and with the wound area under the suspended cover.

2. The wound treatment system of claim 1, wherein an amount of said agent is effective to inhibit bacterial infection of said wound.

3. The wound treatment system of claim 1, wherein the heating element is structured and arranged to heat said medically useful agent to a temperature sufficient to inhibit bacterial infection of said wound.

4. The wound treatment system of claim 1, wherein the medically useful agent is located on the autonomous heating element.

5. The wound treatment system of claim 1, wherein the medically useful agent is located close enough to the heating element to receive radiant heat from the autonomous heating element.

6. The wound treatment system of claim 1, wherein the cover is a transparent or semi-transparent film.

7. The wound treatment system of claim 1, wherein the cover is a transparent or semi-transparent dome.

8. The wound treatment system of claim 1, wherein the medically useful agent is an antimicrobial agent.

9. The wound treatment system of claim 8, wherein the antimicrobial agent is selected from the group consisting of halogenated hydroxyl ethers, acyloxydiphenyl ethers, and combinations thereof.

10. The wound treatment system of claim 1, wherein the medically useful agent is impregnated in a strip of an inert carrier.

11. The wound treatment system of claim 1, wherein the medically useful agent is triclosan impregnated in a strip of melt-spun polymer.

12. The wound treatment system of claim 1, wherein dimensions of the enclosed wound treatment compartment are adjustable to accommodate wounds of different dimensions.

13. A method of wound treatment, comprising:
    enclosing a wound area with a wound treatment system comprising:
    a body structured and arranged to surround a wound area, said body having an opening above the wound area;
    a cover attached to the body and covering the opening, said cover suspended above the wound area;
    said opening and said cover forming an enclosed and empty wound treatment compartment;
    an autonomous heating element incorporated into the body or into the cover; and
    a medically useful agent evaporating or sublimating at an accelerated rate above normal body temperature of about 40° C. to about 80° C.
    said medically useful agent in fluid communication with the compartment,
    activating said heating element, thereby heating said medically useful agent;
    evaporating or sublimating portions of said medically useful agent to cause vapors of said medically useful agent to fill the enclosed wound treatment compartment; and
    contacting said wound area with vapors of said medically useful agent.

14. The method of wound treatment of claim 13, wherein activating of said autonomous heating element provides radiant heat to said wound area.

15. The method of wound treatment of claim 13, wherein the cover is a transparent or semi-transparent film.

16. The method of wound treatment of claim 13, wherein the cover is a transparent or semi-transparent dome.

17. The method of wound treatment of claim 13, wherein the medically useful agent is an antimicrobial agent selected from the group consisting of halogenated hydroxyl ethers, acyloxydiphenyl ethers, and combinations thereof.

18. The method of wound treatment of claim 13, wherein the medically useful agent is triclosan impregnated in a strip of melt-spun polymer.

* * * * *